US006084154A

United States Patent [19]
McCabe et al.

[11] Patent Number: 6,084,154
[45] Date of Patent: Jul. 4, 2000

[54] METHOD FOR GENETIC TRANSFORMATION

[75] Inventors: Dennis E. McCabe, Middleton; Brian J. Martinell, Madison, both of Wis.; Donald A. Glaser, Berkeley, Calif.

[73] Assignee: PowederJect Vaccines, Inc., Madison, Wis.

[21] Appl. No.: 07/858,818

[22] Filed: Mar. 27, 1992

Related U.S. Application Data

[60] Division of application No. 07/422,921, Oct. 17, 1989, Pat. No. 5,120,657, which is a continuation-in-part of application No. 06/938,570, Dec. 5, 1986, abandoned, and a continuation-in-part of application No. 07/193,357, May 12, 1988, Pat. No. 5,015,580, which is a continuation-in-part of application No. 07/079,658, Jul. 29, 1987, abandoned.

[51] Int. Cl.$^7$ ........................... C12N 15/82; C12N 15/87; C12N 15/90
[52] U.S. Cl. .......................................... 800/293; 435/470
[58] Field of Search .................................. 435/172.3, 287, 435/470; 935/85; 800/293

[56] References Cited

U.S. PATENT DOCUMENTS

| | | | |
|---|---|---|---|
| 3,069,809 | 12/1962 | Simmons | 47/57.5 |
| 3,552,653 | 1/1971 | Inoue | 239/81 |
| 3,942,531 | 3/1976 | Hoff et al. | 128/328 |
| 4,302,670 | 11/1981 | Zaderej | 250/324 |
| 4,945,050 | 7/1990 | Sanford et al. | 435/172.1 |
| 5,120,657 | 6/1992 | McCabe et al. | 435/287 |

FOREIGN PATENT DOCUMENTS

| | | |
|---|---|---|
| 0164575 | 12/1985 | European Pat. Off. . |
| 0257472 | 3/1988 | European Pat. Off. . |
| 0270356 | 6/1988 | European Pat. Off. ......... C12N 15/00 |
| 0275069 | 7/1988 | European Pat. Off. . |
| 0286429 | 10/1988 | European Pat. Off. . |
| WO 8501856 | 5/1985 | WIPO . |
| WO 8605516 | 9/1986 | WIPO . |

OTHER PUBLICATIONS

Sanford, et al., "Delivery of Substances Into cells and Tissues Using a Particle Bombardment Process," *Particulate Science and Technology* 5:1:27–37 (1987).
Sanford, "The Biolistic Process," *Tibtech* 6:299–302 (1988).
Klein, et al., "High–Velocity Microprojectiles for Delivering Nucleic Acids Into Living Cells," *Nature* 327:70–73 (May 7, 1987).
Klein, et al., "Particle Gun Technology: A Novel Method For the Introduction of DNA into Living Cells," Poster #28 Biotechnology In Plant Science: Relevance to *Agriculture in the Eighties*, Jun. 23–27, 1985.
Johnston, "Biolistic Transformation: Microbes to Mice," *Nature* 346:776–777 (1990).
McConchie, et al., "The Male Germ Unit and Prospects for Biotechnology," *Biotechnology and Ecology of Pollen*, (Jul. 9–11, 1985) pp. 289–296, Potrykus, "Gene Transfer to Cereals: An Assessment," *Biotechnology*:535–452 (Jun. 1990).
Korohoda, et al. "High–Efficiency Genetic Transformation in Maize Induced By Exogenus DNA," *Z. Pflanzenphysiol.Bd.* 94:95–99, (1979).
Hess, "Attempts to Transfer Kanamycin Resistance of Bacterial Plasmid Origin in Petunias Hybrida Using Pollen as Vectors," *Biochem. Physiol. Pflanzen.* 176:322–328 (1981).
Sanford, et al., "Attempted Pollen–mediated Transformation Using Ti–Plasmids," *Biotechnology and Ecology of Pollen* (1985) pp. 71–76.
Ohta "High–efficiency Genetic Transformation of Maize by a Mixture of Pollen and Exogenous DNA," *Proc. Natl. Acad. Sci.* 83:715–719 (1986).
Hepher, "Micro–injection of DNA into Pollen, Ovaries and Somatic Cells," *Genetic Engineering of Plants and Microorganisms Important for Agriculture*, p. 32–33 (1985).
Graves, et al., "The Transformation of *Zea mays* Seedlings with *Agrobacterium tumefaciens*, " *Plant Molecular Biology*, 7:43–50 (1986).
Fraley, et al., "Expression of Bacterial Genes in Plant Cells," *Proc. Nat. Acad.* 80:4803–4807 (Aug. 1983).
Fromm, et al., "Expression of Genes Transferred into Monocot and Dicot Plant Cells by Electroporation," *Proc. Natl. Acad. Sci.* 82:5824–5828 (Sep. 1985).
Flavell, et al, "Prospects for Transforming Monocot Crop Plants," *Nature* 307:108–109.
Moynahan, et al., "Development of Jet Injection and its Application to Intra–lesional Theraphy in Dermatology," *British Medical Journal*, p. 1541–1543 (1965).
Wastie, "Innoculating Plant Material by Jet Injection," *Plant Pathology* 33:61–63 (1984).
LaChapelle, et al., "Tatouages Permanents Consecutifs A Des Injections Par Dermo–Jet . . . ," *Ann. Dermatol. Venereol.* 109:939–946 (1982).
De Wet, et al., "Gametophyte Transformation in Maize," *Biotechnology and Ecology of Pollen*, (Jul. 9–11, 1985) pp. 59–64.
Sanford et al 1987 Particulate Science and Technology 5:27–37.
Christou et al 1988 (Apr.) Plant Physiol 87:671–674.
Klein et al 1987 Nature 327:70–73.
Weast et al 1966 Handbook of Chemistry and Physics 47$^{th}$ Edition CRC Press pp. F–31, 40–41, and 123.

*Primary Examiner*—David T. Fox
*Attorney, Agent, or Firm*—Thomas P. McCracken

[57] ABSTRACT

A method and apparatus is disclosed for the genetic transformation of organisms by accelerated particle mediated transformation. Foreign genes are introduced into cells by coating on carrier particles which are physically accelerated into the cells. The treated cells are recovered, and a portion of them will contain in their genome the foreign gene. The procedure may be used to create genetically engineered organisms of many types.

4 Claims, 6 Drawing Sheets

METHOD FOR GENETIC TRANSFORMATION

CROSS-REFERENCE TO RELATED APPLICATIONS

This application is a divisional of Ser. No. 07/422,921 filed Oct. 17, 1989, now U.S. Pat. No. 5,120,657 which is a continuation-in-part of Ser. No. 06/938,570 filed Dec. 5, 1986 now abandoned and a continuation-in-part of Ser. No. 07/193,357 filed May 12, 1988, now U.S. Pat. No. 5,015,580, which application was a continuation-in-part of Ser. No. 07/079,658 filed Jul. 29, 1987, now abandoned.

FIELD OF THE INVENTION

The present invention relates to the general field of genetic engineering of plants and other organisms and relates, in particular to the transformation of exogenous genetic material into an organism by physically introducing the genetic material into the organism.

BACKGROUND OF THE INVENTION

There exists much current effort and research being expended toward the genetic transformation of plant species. It is believed that the development of efficient means for transforming foreign genes into plant germ lines will allow the diversity of the genetic stock in commercially important crop species to be widened and to allow functional genes of specific interest to be selectively introduced into crop species. The effort and research to date on the transformation, or genetic engineering, of plant species has achieved results which vary quite dramatically depending on the species of plant.

The principal mechanism which has been used heretofore for the introduction of exogenous genes into plants has begun with the transformation of single plant cells either as protoplasts or in an undifferentiated tissue mass known as a callus. Chimeric genes functional in plant cells have been introduced into single cell plant protoplasts by electroporation and microinjection. However, the most widely used transformation technique used to date has taken advantage of a natural trait of the Plant Pathogen *Agrobacterium tumefaciens*, which has the innate ability to transfer a portion of the DNA from a Ti (Tumor-inducing) plasmid harbored in it into an infected plant cell. By inserting foreign genes into plasmids in Agrobacterium which carry certain sequences from the Ti plasmid, the bacterial transformational trait can be used to transport the foreign genes into the genome of the infected plant cells. Agrobacterium-mediated plant cell transformation has been found to work reasonably well in many model crop species, such as tobacco, petunia and carrot, but does suffer from two significant limitations. The first limitation is that the mediation can only be done on an individual cellular level, typically with somatic tissues, which then must be regenerated artificially into a whole plant. This limits the applicability of Agrobacterium-mediated genetic transformation to those crop species which can readily be regenerated from types of tissues which are susceptible to Agrobacterium infection. A second limitation is that the natural host range of Agrobacterium includes only dicotyledonous plants and a limited number of monocot species of the Liliaceae family. Therefore Agrobacterium-mediated transformation has not been proven to be an effective tool for monocot species of commercial interests, such as the cereal crop species.

It has been demonstrated that at least some chimeric gene constructions are effective for expression of foreign genes in most plant cells. The functionality of these chimeric constructions in monocots as well as dicots has been demonstrated by the transformation of maize protoplasts in culture through such techniques as electroporation. However, no currently known methodology exists to regenerate whole maize plants, or whole plants of any other important crop species, from such protoplasts. No whole, intact transformed maize plants, for example, are known to have been generated. Nevertheless genetic transformation of lines of maize and other crop species is a desired objective because of the great agricultural value of the common crop plants and the potential to improve their value and productivity.

There has been at least one suggestion previously that maize plants can be genetically transformed by genetic transformation of their pollen. Published PCT patent application WO 85/01856 to DeWet purportedly describes a method for the transfer of exogenous genes into flowering plants by transforming the pollen of the plants. Attempts by others to verify this technique and reproduce the experiment have failed. Sanford et al., *Theor. Appl. Genet.*, 69 (5–6), 571–74 (1985). A report of one similar result has been made. Ohta, *Proc. Natl. Acad. Sci. USA*, 83:715–719 (1986).

SUMMARY OF THE INVENTION

The present invention is summarized in that an apparatus for injecting carrier particles carrying DNA into living cells includes a spark discharge chamber, two electrodes extending into the spark discharge chamber and spaced apart by a spark gap, the electrodes adapted for attachment to an external source of high voltage discharge, a carrier sheet held spaced above the spark discharge chamber in a fashion such that it may be vertically moved, the carrier sheet receiving the carrier particles thereon; a retaining screen fixed in place above the carrier sheet; and a target surface held spaced above the retaining screen and carrying the cells so that a spark discharge generating a shock wave in the discharge chamber will accelerate the carrier sheet into the retaining screen so that the carrier particles are accelerated into the cells on the target surface.

The present invention is also directed toward a method for using this apparatus to propel genetic material into living cells.

The present invention is further directed toward the genetic transformation of important crop plants through genetic transformation.

It is an advantage of the present invention in that the apparatus is relatively quick and efficient, and easy to use.

It is an advantage of the process of the present invention and the materials produced therefrom that foreign genetic material, characterized or uncharacterized, can readily and rapidly be introduced into many living organisms.

An additional advantage of the process of the present invention is that numerous transformant events are possible and feasible because of the relative ease of performing the process, in contrast to prior somatic-cell transformation techniques or micro-injection which are difficult to perform, or require cell-by-cell treatment.

Other objects, advantages and features of the Present invention will become apparent from the following specification when taken in conjunction with the accompanying drawings.

DETAILED DESCRIPTION OF THE INVENTION

In the practice of accelerated particle plant or other organism genetic transformation conducted in accordance with the present invention, DNA is physically delivered into the cytosol of cells of the organism, the DNA being carried on individual small particles of biologically inert material which are accelerated at the cells so that the particles enter the individual cells but neither destroy nor incapacitate them. It has been found that DNA delivered in such a fashion will be incorporated into the genetic material of the progeny of the cells. Thus, transforming cells in this fashion allows for the genetic engineering of plants and other organisms. The procedure and apparatus have been used to genetically engineer plants through pollen or meristem transformations and also a variety of other organisms' cells including microorganisms, yeast and invertebrate and vertebrate animal cells.

There are several factors which influence successful pollen-mediated transformations. The manner in which the particles are accelerated is preferably carefully arranged so that the individual DNA-bearing particles have a proper momentum and velocity, and the particles themselves are in a relatively uniform pattern, when contacting the pollen that they penetrate a significant number of pollen cells without biologically disabling them. Furthermore, the DNA on the particles should be stable and capable of transforming plant cells and expressing the desirable trait in the plant cells. In addition, the DNA itself may contain a selectable marker which can be detected in putatively transformed plant seeds or plantlets in order to verify the specific plants in which genetic transformation has occurred. If the transformation frequency is high enough, such a selectable marker may not be necessary.

Figure 1:
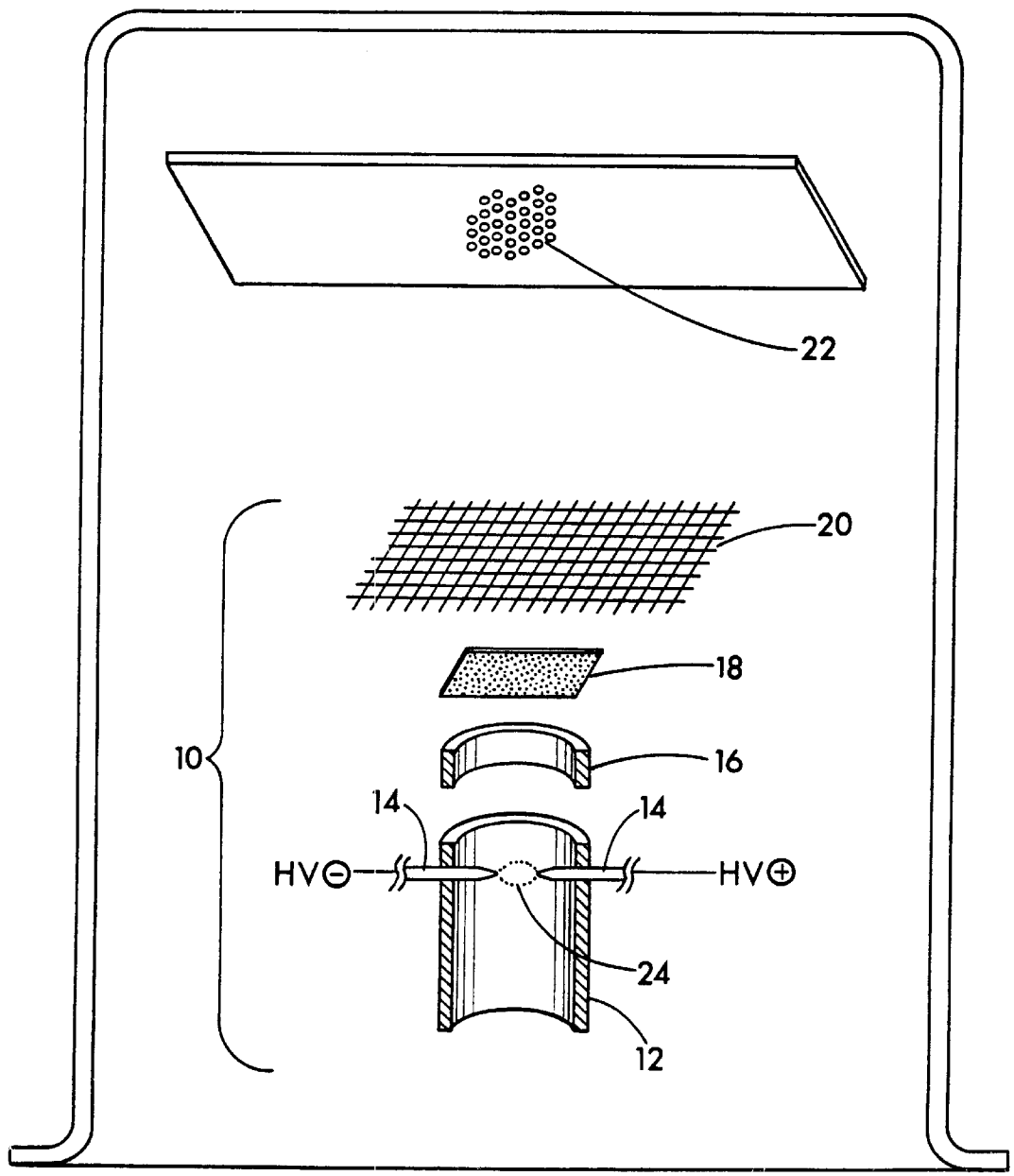
FIG. 1 is an exploded perspective view of a first embodiment of an apparatus constructed in accordance with the present invention.

There are many types of mechanical systems which can be envisioned to accelerate biologically inert small carrier particles. Possible mechanisms might include ballistic explosive acceleration of particles, centrifugal acceleration of particles, electrostatic acceleration of particles or any other analogous system capable of providing momentum and velocity to small inert particles. One novel method preferred by the applicants here is illustrated in schematic fashion in FIG. 1. The method illustrated here makes use of a shock wave created by high voltage electrical discharge. In FIG. 1, and generally indicated at 10, is an accelerator for accelerating the inert particles using this method. Also shown in FIG. 1, and generally indicated at 22, is a target surface for carrying the pollen target thereon.

The accelerator 10 consists of several parts. A spark discharge chamber 12 has provided extending into its interior a pair of electrodes 14. The geometry of the spark discharge chamber 12 is not believed to be critical to the present invention as long as the chamber is configured to develop and present a shock wave of proper character and proper direction that it can be used to propel the carrier particles. The applicants have found that a section of 13 millimeter interior diameter polyvinyl chloride plastic pipe is satisfactory for use as the spark discharge section 12. The electrodes 14 are extending oppositely into the interior mounted approximately 5 millimeters below the top of the spark chamber 12. The electrodes 14 themselves are formed by threaded bolts extending into suitable threads formed in the interior sidewall surfaces of the spark chamber 12 wall itself. The ends of the threaded bolts forming the electrodes 14 are protected with an arc resistant alloy obtained from high electric voltage relay contact points cut to a size of approximately 2 millimeters by 2 millimeters by 3 millimeters and soldered to the ends of the threaded bolts. The gap between the electrodes 14 can be adjusted by appropriately threading the bolts into or out of the spark chamber 12. The preferred gap for discharge voltage of approximately 15 kilovolts between the ends of the electrodes is between 1 and 1.5 millimeters. The method of fabricating and mounting the electrodes 14 themselves is clearly subject to wide variation, although it is preferred that the electrodes be highly durable and that the distance of the spark gap between the electrodes be readily adjustable.

A spacer ring 16 is provided above the spark chamber 12. The spacer ring. 16 may be constructed out of the same PVC pipe as the spark chamber 12 itself and preferably be cut to a vertical length of 6 millimeters. In a fixed apparatus for transformations of a single crop species, the spacer ring 16 could be constructed merely as a vertical extension of the spark discharge chamber 12, although a removable and replacable spacer ring 16 allows adjustment of the distance from spark discharge to carrier sheet to be varied so that the force of particle acceleration can be varied by conditions or by species. The spacer ring 16 may be left open at the top if a large carrier sheet 18 is used, but may also advantageously have its top opening partially restricted by a suitable closure to form a rectangular opening approximately 9 by 13 millimeters. Placed atop the spacer 12 is a carrier sheet 18. The carrier sheet 18 is a planar, light sheet formed of suitable size to be placed resting atop the spacer ring 16. The carrier sheet 18 is formed of flexible biologically inert sheet material capable of carrying biologically inert small particles thereon. The carrier sheet 18 functions to transfer the force of a shock wave from a spark discharge into acceleration of the carrier particles. It has been found that the carrier sheet 18 may advantageously be formed from 1 mil or 0.5 mil plastic coated aluminized mylar, with the 0.5 mil sheets being preferred since in practice they result in better penetration into the pollen. As a general practice the smaller the actual surface area of the carrier sheet 18, the better penetration is obtained by the carrier particles into the pollen. This consideration regarding penetration is balanced by the need to have the carrier sheet of a size which is easy to handle and which provides an impact pattern over a large enough field to be able to impact large numbers of pollen cells in each individual injection. A carrier sheet size of 9 by 11 millimeters has been found to provide a good size yielding good penetration in a desirable impact pattern of the particles onto the pollen target.

The carrier sheet also functions to arrange the pattern of the particles as they contact the target surface. An even uniform pattern of particles is highly desirable to ensure that as many cells on the target as possible are impacted, in order to maximize the yield of transformants. Non-transformed cells, pollen or otherwise, may be at a competitive advantage with transformants or may be partially debilitated by the carrier particles. Therefore it is desirous to reach as close to 100 percent injection into the target cells as is possible, and a uniform layer and pattern of particles on a carrier sheet 18 aids this objective.

As to the carrier particles themselves, any high density material which is biologically inert should be acceptable for use as the DNA carrier particles within the context of the present invention. Metallic materials are preferred, such as tungsten and gold, which have a density of 19. Iridium might also be preferable, having a density value of 22, but has not been used by the applicants because it is only easily available in a relatively course powder. Tungsten is also probably less desirable compared to gold because it tends to oxidize in air in the presence of even trace moisture. Such an oxidation layer on the carrier particles tends to bind the particles together causing severe increase in average particle size as the particles aggregate together. Particles which are clumped in irregular aggregations are less desirable for the practice of the present invention since such aggregations will vary widely in their mass and size, thus leading to difficulty in obtaining regularly replicable results. It has been found that gold is an optimal material for the particles within the present invention since it has high density, is relatively inert to both biological materials and to oxidation, and is readily commercially available in the form of spheres having a diameter of 0.2 to 3 micrometers. Gold spherical particles, or beads, in a size range of 1–3 microns have been successfully used in the apparatus as well as gold sold as a microcrystalline powder which has, by actual measurement, been found to have a size range of 0.2 to 3 microns. Suitable DNA sequences may be applied to the gold particles and the gold particles may be applied to the carrier sheet in a manner which will be discussed in further detail below.

Located above the carrier sheet 18 is a retainer screen 20. The retainer screen 20 is a 100 mesh stainless steel screen physically mounted in a plastic holder approximately 5 millimeters above the top of the spacer ring 16. The retainer screen 20 functions to restrain the carrier sheet 18 so that it does not proceed to the target.

The target surface 22 is a planar sheet of material capable of suspending the target cells, i.e. pollen or other plant cells, thereon. In practice it has been found that an easily useable target is a petri dish 60 millimeters by 15 millimeters inverted over the top of the assembly holding the retainer screen. Spacing from the retaining screen 20 to the target cells on the target surface 22 is therefore preferably approximately 15 millimeters. Spacing greater than 15 millimeters, under the conditions of voltage and atmospheric pressure described below, loads to reduced penetration of carrier particles into the pollen while a spacing of less than 5 millimeters results in crushed cells in the event that the retaining screen 20 deforms under the force of the blast.

If pollen is used as the target cells, the pollen must be applied to the target in such a fashion that the target may be inverted with the pollen remaining viable. Since pollen in general is sensitive to moisture, the method used to adhere the pollen to the target should be as moisture-free as possible. It has been found that mineral oil is useful as such an adhesive. If a thin layer of mineral oil is applied to the bottom of a Petri dish to be used as the target surface 22, pollen is dusted into the dish, and then the dish overturned to remove excess pollen, it has been found that a relatively uniform monolayer of pollen grains remains on the target which will remain in place during particle injection and which remains viable. If cells other than pollen are used in this apparatus other support media or adhesives, such as agar or parafin, may be more appropriate. For other tissues from a plant or any other organism, the nature of the target surface may vary as appropriate. For somatic cell transformations, live animals may be placed on the target surface. For microorganisms, any thin culture medium may be used. All that is required is a physical arrangement to maintain the target organism or organisms in place physically over the apparatus and at a proper distance in the line of flight of the particles.

The entire assembly of the particle accelerator 10 and the target surface 22 may be partially evacuated so as to prevent the force of atmospheric drag from slowing the particles and/or the carrier sheet 18. The vacuum should be only a partial vacuum since a high vacuum would desiccate the target pollen cells, rendering them non-viable. A vacuum of 460 to 480 millimeters of mercury has been found sufficient and advantageous.

In the simplest explanation of the operation apparatus of FIG. 1, the process of firing the accelerator 10 begins with the placement of a drop 24 of distilled or demineralized water between the electrodes 14. The amount of water must be selected so as not to dampen the arc which will occur between the electrodes but yet be of sufficient volume to create a shock wave in the interior of the spark chamber 12 when the discharge does occur. The preferred volume of water has been found to be approximately 2–4 microliters. This amount of water may be applied by pipette suspended between the ends of the electrodes 14. The water droplet 24 will bridge the gap between the electrodes and remain in place.

The spacer ring 16 is then placed upon the top of the spark chamber 12 and the carrier sheet 18 is placed on the top of the spacer ring 16. The retaining screen 20 is mounted in place 5 millimeters above the carrier sheet 18 and the target surface 22 consisting of the overturned Petri dish is placed above the mounting of the retaining screen 20. The assembly is then evacuated to 480 millimeters of mercury.

External to the apparatus illustrated in FIG. 1, a voltage supply is connected to generate 15,000 volts DC. The 15,000 volts DC is then applied to a 1 microfarad capacitor, which is then disconnected from the voltage source. By throwing a suitable switch, the 15,000 volt charge on the capacitor is then applied between the electrodes 14.

When the voltage is applied, an electric discharge are jumps between the two electrodes 14. The arc instantly vaporizes the small water drop extending between the electrodes. A shock wave from the explosive vaporization of the water drop propagates throughout the interior of the spark chamber 12. When the shock wave reaches the carrier sheet 18, the carrier sheet 18 is lifted vertically off the spacer ring 16 and is accelerated toward the retaining screen 20. When the carrier sheet 18 hits the retaining screen 20, the carrier sheet 18 is restrained in place and the particles carried on the carrier sheet 18 leave the carrier sheet and fly freely across the distance to the cells resting on the target surface 22. If the apparatus has been properly constructed and adjusted, and the procedure properly followed, a significant percentage of the carrier particles will arrive at the target with a correct velocity to penetrate the cells carried on the target surface 22, without destroying an unacceptable percentage of the cells. The cells on the target surface 22 may than be removed from the target surface 22 and selected as appropriate to segregate transformants from non-transformants. If pollen is used in the process, the pollen is then removed from the target surface 22 and hand pollinated onto fertile female flowers, such as maize silks, which will then set seed, or kernels. The seed can be harvested, planted and evaluated for the morphological or biochemical traits conditioned by the DNA carried on the carrier particles into the pollen. Alternatively, immature embryos may be excised from the developing seed tissues and the embryos grown out in appropriate tissue culture into small plantlets or into whole plants. The plants or plantlets, or tissues from them, can then be tested for selection on the basis of a selectable marker carried in the DNA transformed into the pollen cells. Suitable selectable markers would include exogenous resistance traits, such an herbicide or antibiotic resistance, or dominant morphological traits whose expression can be observed.

It is to be understood that while the apparatus of FIG. 1 has been specifically developed for the process of pollen mediated plant transformation in accordance with the present invention, the apparatus itself is also useful for accelerated particle transformation of other tissue types, and for plant and animal cells as wall. The apparatus allows for easy adjustment of the particle force by varying the spacing or the discharge voltage. It is relatively simple to operate, efficient and stable so that results may be replicated.

Within the preferred process of the present invention, the process for applying the DNA sequences to the particles, the process for layering the particles into the carrier sheet, and the process for preparing the DNA for plant transformation all may require particular attention. Each of these details will be discussed in turn.

The DNA sequence including a foreign gene prepared in the form suitable for plant transformation can be simply dried onto naked gold or tungsten pellets. However, DNA molecules in such a form was thought to have a relatively short period of stability and tend to degrade rather rapidly due to chemical reactions with the metallic or oxide substrate of the particle itself. It was initially found that if the carrier particles were first coated with an encapsulating agent the DNA strands have greatly improved stability and would not degrade significantly even over a time period of several weeks. A suitable encapsulating agent was found to be polylysine (molecular weight 200,000) which can be applied to the carrier particles before the DNA molecules are applied. Other encapsulating agents, polymeric or otherwise, were also believed useful as similar encapsulating agents. The polylysine was applied to the particles by rinsing the gold particles in a solution of 0.02% polylysine and then air drying or heat drying the particles thus coated. Once the metallic particles coated with polylysine were properly dried, DNA strands were then loaded onto the particles. The DNA was loaded onto the particles at a rate of between 3 and 30 micrograms of DNA per milligram of gold bead spheres. The practice was to add to 100 micrograms of DNA and 30 milligrams of 1–3 micron gold spheres precoated with polylysine, sequentially 5 microliters of 10 mM $Na_2 HPO_4$, and then 5 microliters of 10 mM $CaCl_2$. to provide a fine $CaHPO$, precipitate which formed as the solution dries. The precipitate carried the DNA with it onto the beads. Once the beads and the phosphate and calcium chloride solution had been mixed with the DNA, the suspension was dried under a nitrogen ($N_2$) stream with frequent stirring. Once dried the precipitate was immediately resuspended in 100% ethanol for the process of placing the particles onto the carrier sheet.

Subsequent investigations cast doubt as to the need for the encapsulating process. The preferred procedure now begins with 5 milligrams of 1.5 to 3 micron gold beads (a microcrystalline gold) suspended in 50 microliters of water. This is then mixed with 50 micrograms of DNA in up to 100 microliters of water. Then 100 microliters of 0.1 M spermidine (free base) is mixed in followed by 100 microliters of 25% (weight per volume) polyethylene glycol (3,000 molecular weight). To this mixture is then added 100 microliters of 2.5 M calcium chloride added while mixing. The suspension is then gently spun down after which the supernatant is discarded. The solids are then resuspended in 5 milliliters of pure ethanol and briefly sonicated in a bath type sonicator before placement on the carrier sheet.

In applying the particles to the carrier sheet, it is preferred for the successful operation of this procedure to form a uniform and reproducible layer of the carrier particles on the carrier sheet. To do this, the particles cannot be simply dusted onto the carrier sheet, since they tend to aggregate and are thus distributed unevenly in a non-reproducible fashion on the sheet. The carrier particles, with the precipitated coating containing the DNA strands, suspended in 100% ethanol, are applied to the carrier sheet. It has been found that 50 to 500 microliters of a well stirred suspension of the ethanol with the carrier particles can be successfully pipetted onto the mylar sheet in a reasonably uniform and reproducible fashion. The pipetted aliquot of this suspension is then allowed to settle. After the settling period, the meniscus is broken and the excess ethanol is drained away. The residual ethanol is removed by evaporation in a partially opened Petri dish.

This process is intended to place the carrier particles coated with the precipitate containing DNA strands on the mylar carrier sheet. A good median rate which was initially found successful within the present invention was approximately 0.1 milligram of carrier particles carrying the precipitate and DNA applied to a 9 by 11 millimeter area of the carrier sheet. The preferred present range for application of DNA coated particles is 0.00125 to 0.15 milligrams per square centimeter. Such a density of carrier particle application to the carrier sheet gets good survival of cells and also a high penetration of cells by the accelerated particles. The actual acceleration and penetration of the cells by the particles will vary both with the cells size, type and diameter, and the number of carrier particles can obviously be varied to give more or fewer particles per cross-sectional area of the target cells as desired.

The DNA for use within the present invention must be constructed in a vector appropriate for expression of the exogenous gene in the cells of maize, or whatever other plant or other organism is being utilized within the present invention. The DNA sequence can be chimeric, but full intact non-chimeric genes from other plants species or lines of the same species may also be used. Vectors suitable for expression in plants generally must include, besides the coding sequence of the desired exogenous gene, appropriate flanking regulatory sequences such as a suitable promotor capable of promoting transcription and expression in vivo in the target organism cells and a translation terminator capable of signalling the end of transcription or the appropriate processing of the RNA in such a fashion that will allow suitable translation of messenger to produce protein synthesis. It has been previously demonstrated that plant gene promoters capable of causing coding sequence transcription and expression in dicot plant cells are also effective in monocots, such as corn, on a cellular level although with lowered efficiency in some cases. From et al., *Proc. Natl. Acad. Sci. USA*, 82:5824–5828, September 1985. Such promoters include the nopaline synthase promoter from the plant pathogen *Agrobacterium tumefaciens* and the CaMv 35S promoter derived from the cauliflower mosaic virus sequence. A suitable termination sequence effective in plants is the polyadenylation sequence from the nopaline synthase gene of *Agrobacterium tumefaciens*. The plant expression vector may also contain a selectable marker operative in plant cells to allow for selection of transformant plants. The selectable marker may condition a trait which may be assayed biochemically or a phenotypic trait which may be observed in the progeny plant. Clearly if a non-chimeric intact gone, with flanking regulatory sequences, from the same or another plant is used in the present process, chimeric promoter or control sequences are unnecessary and the gene may be used with its native sequence.

The apparatus and method of the present invention will be described in particular detail with regard to pollen-mediated transformation of maize. Nevertheless, it should be understood that there is nothing intrinsic to the apparatus or process that is of necessity limited to maize, and the process is equally suitable for transformation of other organisms of many types. The procedure for handling target tissues of other species may need to be varied and the spacing of the parts of the apparatus critical to carrier particle velocity may need to be varied depending on the organism, but the basic apparatus and procedure may be used in other plant, animal and microbial species.

In addition, while the transformation example described here is directed toward pollen-mediated plant transformation, the apparatus disclosed herein is equally suitable for use in transformation of other plant tissues, such as embryogenic callus or somatic embryos, or any other plant or other non-plant tissue.

Since not all of the pollen will have carrier particles inserted into them, and since not all pollen cells or progeny zygotes will uptake the DNA into their genome, it will be necessary to screen the progeny plants at some stage to select for transformant. If it is desired to transform a given foreign gene into a plant, the gene may be inserted into a chimeric expression vector. The chimeric expression vector could then be transformed into plant cells along with a selectable marker plasmid, such as pCMC 1022 described herein below. The two vectors (foreign gene and selectable market) can be ligated together to make one plasmid, or the two vectors can be cloned separately and then applied together to the same carrier particles. In either event, the progeny produced are screened for the marker to select transformed progeny. While the use of such a selectable marker may be desirable in some circumstances, it may be omitted if a suitable morphological or biochemical test exists to screen for the transformed progeny. A morphological screening test could be for a dominant phenotypic trait in the progeny. A suitable biochemical screening test could be a so-called "Southern" blot hybridizing probe for the existence of the transforming DNA itself in the genome of the progeny plants.

EXAMPLES

1. Construction of Vectors

A. Antibiotic Resistance

Figure 2:
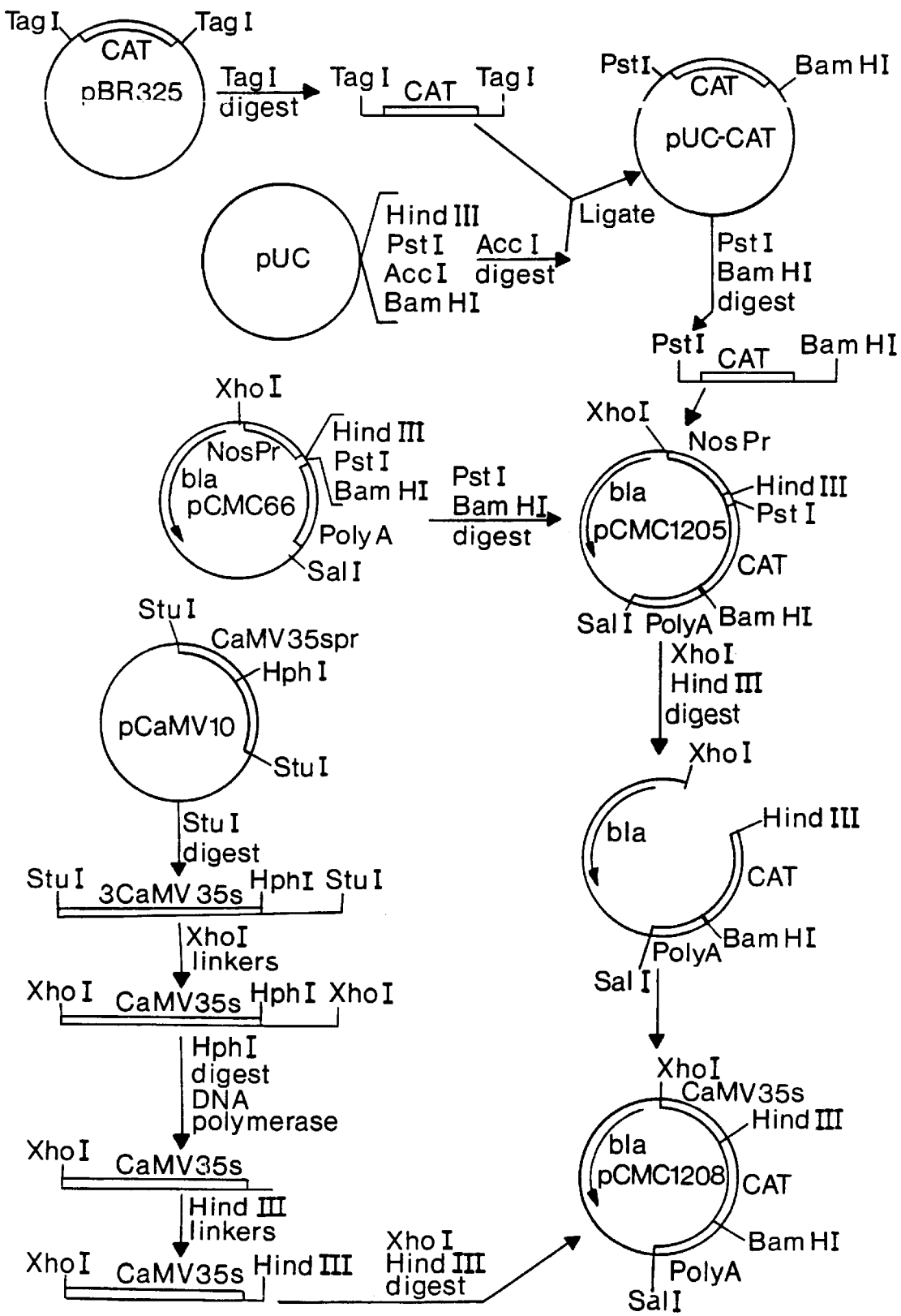
FIG. 2 is a schematic illustration of the plasmid manipulations in the process of making plasmid pCMC 1208.
Figure 3:
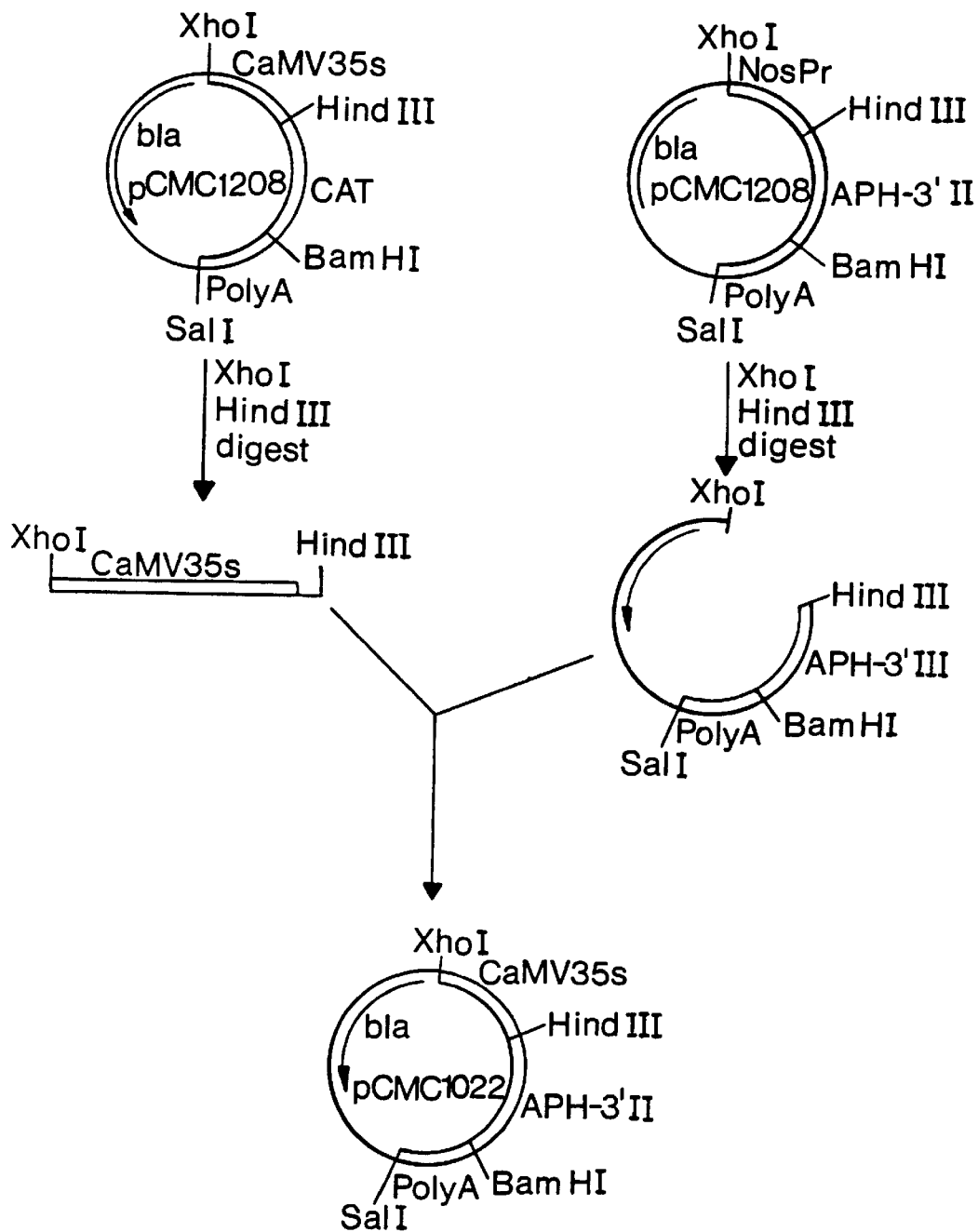
FIG. 3 is a schematic illustration of the plasmid manipulations in the process of making the plasmid pCMC 1022.

The construction of suitable plant expression vectors is illustrated in schematic fashion in FIGS. 2 and 3. FIG. 2 illustrates, in schematic form, the construction of a plant expression vector pCNC 1208. The construction of the plasmid pCMC 1208 began with the digestion of the plasmid pBR 325 (Bolivar, F. *Gene* 4:121–136 (1978)) with the restriction endonuclease Tag I. The plasmid pBR 325 contains a coding sequence for the antibiotic resistance gene chloramphenicol acetyl transferase (CAT) which is existed from the remainder of the plasmid by Tag I digestion. After digestion of pBR 325, the fragments were resolved by electrophoresis in an agarose gel and the fragment containing the CAT gene was excised. The CAT fragment was then ligated into the plasmid pUC 9 (Viera & Messing, *Gene*, 19:259–268 (1982)) which had previously been digested with the restriction enzyme Acc I. The fragment ends produced by Tag I and Acc I are complementary in this case and thus the strands were directly ligatable. The resulting plasmid, designated pUC-CAT in FIG. 2, contained the CAT coding sequence flanked by portions of the polylinker from pUC 9. This plasmid was digested with Pst I and Bam HI, and the smaller of the two fragments was isolated by gel electrophoresis. This fragment was then ligated to an intermediate plant expression vector pCMC 66, which had been previously digested with Pst I and Bam HI, to form the CAT expression plasmid pCMC 1205. The plasmid pCMC 66 contains the nopaline synthase promoter (Nos Pr) from *Agrobacterium tumefaciens* and a nopaline synthase polyadenylation sequence (Poly A), from the same organism, surrounding six plasmid unique restriction sites. The plasmid pCMC 66 also carries a version of the beta-lactamase gone (bla) which expresses resistance to the antibiotic ampicillin in bacteria, so that ampicillin resistance can be used as a selection marker in subsequent recombinations performed in *E. Coli.*

The plasmid pCaMV 10 (Gardner et al., *Nucl. Acids Res* 9:2871–2888(1981)) was digested with Stu I and the fragment containing the cauliflower mosaic virus 35 promoter (CaMv 35s) was joined to synthetic Xho I oligonucleotide linkers. The fragment was then digested with Hph I, treated with a DNA polymerase to generate blunt ends, and then joined to synthetic Hind III oligonucleotide linkers. Digestion of this fragment with both Xho I and Hind III produced a fragment containing the CaMv35s promoter and transcription start site modified at its ends by the addition of the restriction site sequences.

The nopaline synthase promoter was excised from pCMC 1205 by digestion of the plasmid with Xho I and Hind III. The larger of the two fragments thus produced was ligated with the CaMv35s promoter fragment to produce pCMC 1208, a plant expression vector having the CaMv35s promoter, the CAT coding sequence and the nopaline synthase polyadenylation sequence in order. The CaMv35s promoter and poly A sequences served as the flanking regulatory sequences for the CAT coding sequence.

Both of the plasmids pCMC 1205 and pCMC 1208 were tested for activity in maize by electroporation into protoplasts, followed by an assay for CAT activity. Both constructions proved active in maize cells, but pCMC 1208 proved significantly higher in level of activity, and thus was selected for plant transformation experiments.

The plasmid pCMC 1208 was used for the pollen-mediated genetic transformation of maize in the apparatus and process of the present invention. However, it was found that the assay for CAT activity had a high background level in maize tissue and thus the CAT gene was considered not an optimal marker in maize. Accordingly, the plasmid was further manipulated to insert another antibiotic resistance gene, of more selectivity in maize, in the vector in place of the CAT gene, as illustrated in FIG. 3.

The plasmid pCMC 1021 contains the nopaline synthase promoter and the nopaline synthase polyadenylation sequence flanking a coding region for the enzyme aminoglycoside-3-phosphotransferase II (APH 3'II) which conditions for resistance to aminoglycoside antibiotics such as kanamycin. Since electroporation experiments revealed the CaMv35s promoter to be much more effective in maize than the Nos Pr, it was decided to transfer the CaMv35s promoter to pCMC 1021. The CaMv35s fragment from pCMC 1208, as illustrated in FIG. 3, was isolated by digestion with Xho I and Hind III and isolation by electrophoresis. The plasmid pCMC 1021 was also digested with Xho I and Hind III and the larger fragment isolated and ligated with the CaMv 35s fragment to produce pCMC 1022. In plasmid pCMC 1022 the coding sequence from APH3' II is flanked by the regulatory CaKV35s and Nos pA sequences.

The plasmids pCMC 1208 and pCMC 1022 were both demonstrated to be effective for transformation and expression in individual cells of tobacco, cotton, soybean and corn through electroporation transformation and protein assays. Plant cells transformed in culture with the APH 3' II have been demonstrated to be resistant to kanamycin for cotton, soybean and corn cells.

B. Endosperm Color Marker

A plasmid referred to as pMBzRI was obtained which contains an approximately 9.9 kilobase Eco RI fragment of the maize genomic DNA which includes the entire gene encoding the enzyme UDP glucose-flavoroid glucosyl transferase, an enzyme which is required for the synthesis of anthocyanin pigments in corn. The genomic fragment contains extensive both 5' and 3' flanking DNA and thus in expected to include appropriate regulatory sequences effective in maize to express the gone. Since the cloned gone is a full-length copy of the normal, functional maize gene, it would be expected that the cloned gene would be fully active and function appropriately in maize cells.

The enzyme itself, UDP glucose-flavoroid glucosyl transferase, is useful as a selectable marker for genetic transformation in maize because maize lines are available which carry recessive mutations which inactivate the endogenous gene. Since the enzyme is non-essential for plant growth and development, the plants of the mutant lines are normal except for the lack of the red anthocyanin pigments produced in various tissues of wild-type or non-mutant maize plants. Introduction of the wild-type gene into homozygous mutant lines results in the production of the enzyme and thus ultimately the production of anthocyanins, so that transformant plants can be easily identified due to their characteristic color. Thus the plasmid pMBzRI is suitable for use, without modification, as a model expression vector in maize and, when coupled to another gene of interest, as a conveniently screenable transformation marker. This is an example of a potentially useful non-chimeric gene.

2. Transformation of Maize using pCMC 1022

A quantity of 1–3 micron gold spherical beads for use as carrier particles were pre-coated with polylysine by being rinsed in 0.02% polylysine and air drying. 100 micrograms of pCMC 1022 DNA in aqueous solution had added to it 33 mg coated beads, and then sequentially 5 microliters of 10 mM $Na_2$ $HPO_4$, and 5 microliters of 10 mM $CaCl_2$ which formed a fine precipitate as the solution was dried in a $N_2$ stream. The dried precipitate-coated beads were then resuspended in 100% ethanol and deposited onto 2.0 mil plastic coated aluminized mylar sheets approximately 1 cm by 1 cm. The coated beads were applied to give a final density of 0.1 mg/cm$^2$ on the mylar carrier sheet.

The carrier sheet carrying the coated beads thereon was mounted atop the spacer 16 in the apparatus of FIG. 1. Pollen was gathered by hand from Early Sun-Glo sweet corn. The bottom of a 60 mm Petri dish was lightly coated with mineral oil and pollen was dusted onto it. Excess pollen was removed by inverting the Petri dish to leave a monolayer. The Petri dish was used as the target surface 22 in the apparatus of FIG. 1.

A vacuum of 55–60 mm of Hg measured with a nanometer, or 500 mm by barometric gauge, was applied to the assembled apparatus of FIG. 1. A 15 KV discharge from the 1 microfarad capacitor was discharged through the electrodes 14 accelerating the coated particles at the pollen on the target surface 22.

The process of preparing beads and pollen and firing the apparatus of FIG. 1 was repeated several times until an adequate supply of treated pollen was accumulated. The treated pollen was brushed off the bottom of the Petri dish with a brush and hand pollinated onto the silks of female plants of Kaltenberg 390 and CFS 5504 hybrids. The silks were physically segregated from other pollen.

From the ears pollinated in this fashion, 52 kernels were produced. The immature embryos were excised from the ears 14 days after pollination and placed in culture on a corn embryo tissue culture medium containing 50 parts per million Kanamycin. The seedlings which grew up on the medium were assayed directly for APH3' II activity and three seedlings assayed positive, indicating the APH3' II enzyme was being expressed in the tissues of the seedling thus indicating successful transformation of these plants.

One of these plants was placed on a nonselective medium before transfer to a greenhouse for further growth. Leaf tissue was analyzed for continued APH3' II activity which was positive.

Another replicate using identical procedures with pollen from A188 and a Flint maternal plant again resulted in progeny from which a plant was selected at random for analysis. The leaves of this plant tested positive for APH 3' II and also evidenced a 4.0 kb fragment in the Southern blot analysis.

Two additional replicates were done utilizing the identical procedure as described above with pollen from CFS 5504 plants placed on silks of CFS 5504 plants. Two plants generated from the procedure were selected at random from the plants produced, and were assayed for APH3' II and were analyzed by Southern blot. Both plants failed to show APH3' II activity but evidenced the 4.0 kb hybridizing fragment in their genome.

The presence of pCMC 1022 sequences in the DNA isolated from these plants and from one plant which did not assay positive was demonstrated by the Southern hybridization-technique. Southern, *J. Mol. Bio.*, 98:503–577 (1975). DNA was isolated from control and test corn leaf samples by micromodification of the cetyl-trimethylammonium bromide procedure of Taylor and Powell, *Focus,* 4:4–6 (1982). 10 micrograms of each DNA sample was digested with the restriction enzymes Ava I and Hind III, resolved by electrophoresis in an agarose gel, transferred to a nylon membrane, and hybridized with a $^{32}$P-labeled probe corresponding to the non-coding strand of the APH II coding region. After washing the filter, hybridizing DNA fragments were visualized by auto radiography.

The expected 1 kb fragment was not found in either plant. However, each of the plants exhibited an approximately 4 kb fragment which hybridized with the APH-3' II probe and which was not found in any of the control non-transformed control samples of maize DNA. One of the two plants (the one positive for APH II) also exhibited a 3.7 kb specifically hybridizing fragment. The fact that the observed fragment is not the expected size is not too surprising since complex restriction patterns are generally observed for DNA transfected into plant and animal cells. Perucho et al., *Cell,* 22:309–317 (1980); Kiens et al., *Plant Mol. Biol.,* 5:223–224 (1985); Paszkowski et al., EMBO J., 3:2717–2722 (1984); Riggs and Bates *Proc. Natl. Acad. Sci.*

USA, 83:5602–5606 (1986). Furthermore, in eucaryotic cells DNA can be modified, e.g. by methylation, in ways that alter its expected restriction digestion pattern. Chandler and Walbot, *Proc. Natl. Acad. Sci. USA*, 83:1767–1771 (1986). Both Ava I and Hind III, the restriction endonucleases used in this example, are known to be inhibited by specific methylation within their recognition sequences. McClelland and Nelson, *Nucleic Acids Res*, 13:r201–r207 (1985). The 4 kb fragment length is equivalent to the plasmid unit length of the pCMC 1022 plasmid and suggests that these plants contain tandemly duplicated copies of the plasmid. Digestion with either enzyme alone would then produce the plasmid-length fragments observed. The 3.7 kb fragment appears to result from a rearrangement of the plasmid, perhaps at its juncture with indigenous maize DNA.

3. Use of pCMC 1022 with other Genes

To transform other genes of interest into maize or other plants, plasmid pCMC 1022 may be used in any of several ways. The APH3' II coding sequence can be deleted by digestion of pCMC 1022 with Hind III and Bam HI and another gene sequence of interest prepared with appropriate ends can be ligated in its place. If the gene of interest can reasonably be selected for, the plasmid may then be directly used for transformations. If the gene of interest is separately prepared with appropriate regulatory sequences, and a selectable marker is desired, the gene of interest with its regulatory sequences can be inserted in any of the sites in the polylinker upstream of the CAMv35s sequence in pCMC 1022. Another alternative to make use of the pCMC 1022 selectable marker is to prepare the gene of interest, in pCMC 1022 or in any other plant expression vector, and to coat pCMC 1022 and the gene expression vector together onto carrier particles as disclosed herein for transformation into plant cells.

The plasmid pCMC 1022 was deposited with the American Type Culture Collection, 12301 Parklawn Drive, Rockville, Md., USA, on Nov. 14, 1986 under ATCC accession No. 67269.

The above deposit was made pursuant to a contract between the ATCC and the Cetus Corporation, a partner in the assignee of the present invention. The contract with the ATCC provides for permanent availability of the progeny of these cell lines to the public on the issuance of the US patent describing and identifying the deposit or the publication or laying open to the public of any US or foreign patent application, whichever comes first, and for availability of the progeny of these cell lines to one determined by the U.S. Commissioner of Patents and Trademarks to be entitled thereto according to 35 USC Section 122 and the Commissioner's rules pursuant thereto (including 37 CFR Section 1.14 with particular reference to 886 O.G. 638). The assignee of the present application has agreed that if the cell lines on deposit should die or be lost or destroyed when cultivated under suitable conditions, they will be promptly replaced on notification with a viable culture of the same cell line.

The present invention is not to be limited in scope by the microorganisms deposited, since the deposited embodiment is intended as a single illustration of one aspect of the invention and any microorganisms which are functionally equivalent are within the scope of this invention. Indeed, various modifications of the invention in addition to those shown and described herein will become apparent to those skilled in the art from the foregoing description and fall within the scope of the appended claims.

It is also to be understood that all base pair sizes given for nucleotides are approximate and are used for purpose of description.

Figure 4:
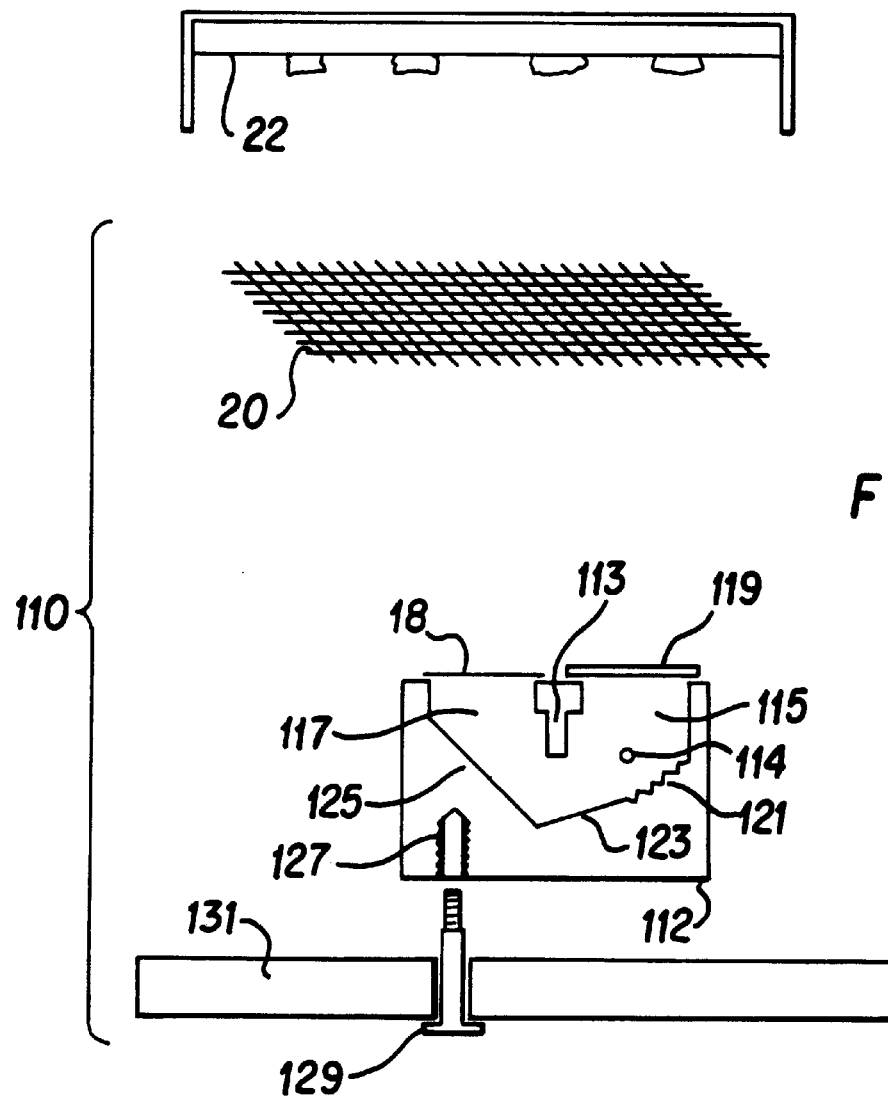
FIG. 4 is an exploded sectional view of a second embodiment of a particle accelerator according to the present invention.
Figure 5:
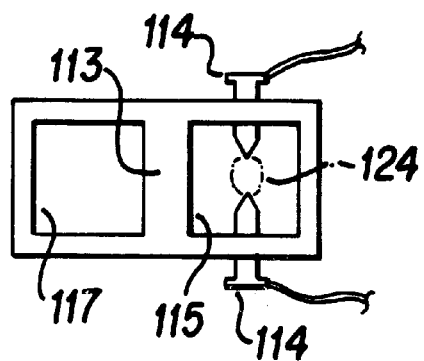
FIG. 5 is a top plan view of the discharge chamber of the accelerator of FIG. 4.
Figure 7:
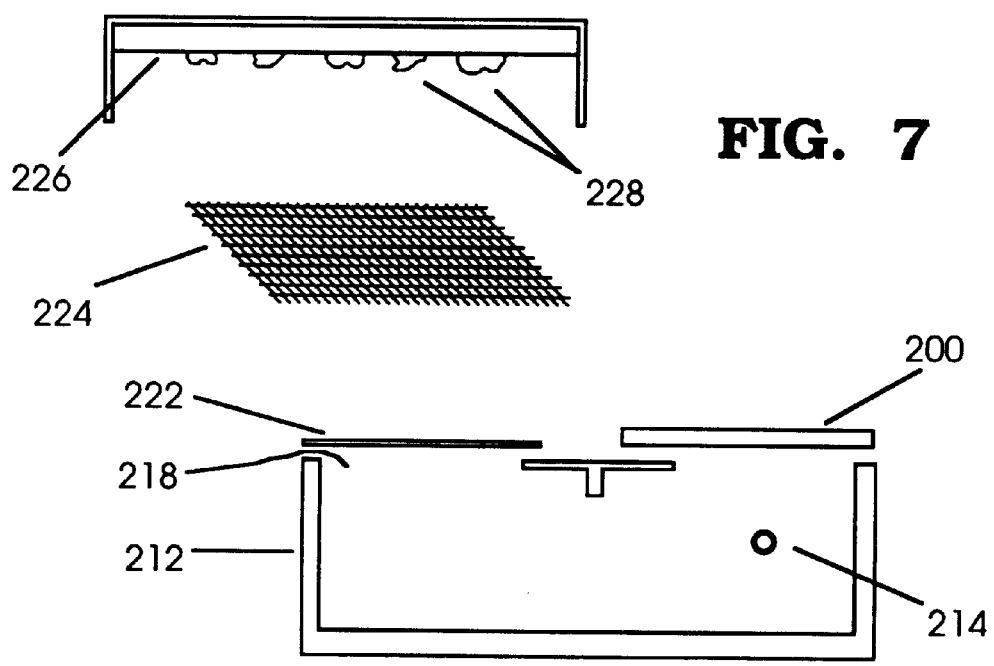
FIG. 7 is an exploded view of yet a third embodiment of a particle accelerator according to the present invention.

Shown in FIGS. 4–5 is an alternative, and improved, embodiment of a particle accelerator 110. In the accelerator 110, there is a discharge chamber 112 into which two electrodes 114, extend. The electrodes 114 are simple threaded steel bolts, without alloy ends, with a gap of about 2 mm between them, which may be oiled with refrigerant or other light machine oil and bridged by a water droplet 124 of about 6 to 10 microliters. The discharge chamber 112 itself is, however, significantly different in geometry from the discharge chamber 12. The discharge chamber 112 is divided by a shield 113 into two subchambers 115 and 117. The subchamber 115, into which the electrodes 114 extend, is where the electrical spark discharge actually takes place. The subchamber 115 has a removable access cover 119, and a bottom surface including a series of steps 121 and a deflector surface 123 angled, at about 20° from vertical, toward the subchamber 117. The subchamber 117 has its top covered by the carrier sheet 18, identical to that described in conjunction with the embodiment of FIG. 1, and has a bottom deflector surface 125, angled at about 45° from vertical, forming much of its bottom surface. A threaded bore 127 in the bottom of the accelerator 110 allows it to be secured by a threaded bolt 129 to a mounting plate 131. The retainer screen 20 and the target surface 22 are identical to those used in the accelerator 10 of FIG. 1, with the preferred spacing being about 20 mm between the top of subchamber 117 and the screen 20, the screen 20 being, in turn, about 5–10 mm from the target 22. Later experimentation revealed that the steps 121 and the deflector surface 125 are probably unnecessary and the discharge chamber 112 can have its interior in a simple box-like shape as illustrated by the embodiment of FIG. 7.

The accelerator 110 operates in a fashion similar to the accelerator 10. The accelerator 110 is intended to minimize shock wave impact to the plant tissues being transformed. The shock wave from the discharge between the electrodes 114 is inertially confined and reflected by the access cover 119. The shield 113 directly shields the carrier sheet 18 and the target 22 from the direct blast or shock wave from the spark discharge. Instead, the blast wave from the discharge is reflected off of the 45° angle of the deflector surface 125 upward at the carrier sheet 18, thus providing a vertical impulse to the sheet 18 while shielding it from the direct shock wave. The preferred spacing from the top of the subchamber 117 to the retaining screen 20 is about 20 mm so that the carrier shoot 18 has an opportunity to amply accelerate.

Figure 6:
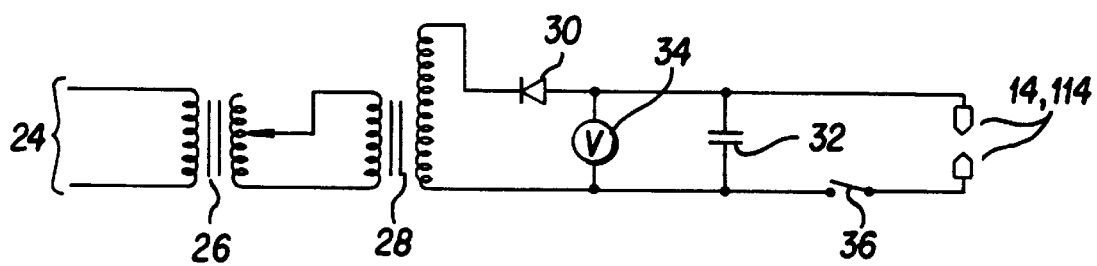
FIG. 6 is a circuit diagram of an electrical discharge circuit for use with the apparatus of FIGS. 1 and 4–5.

Shown in FIG. 6 is a circuit for use in creating an electrical discharge for either of the accelerators 10 or 110. Connected to AC power 24 is one coil of a variable transformer 26. The output of the variable transformer is connected to the input of a step-up high voltage transformer 28. The high voltage output of the transformer 28 is connected through a high-voltage silicon rectifier 30 to apply a DC-voltage to a high-voltage 2 microfarad capacitor 32. A voltmeter 34 is connected across the capacitor to monitor its voltage. A switch 36 connects the output of the capacitor 32 through the electrodes 14. The use of the variable transformer 26 allows the DC voltage which accumulates in the capacitor 32 to be adjusted as desired to vary the force of the blast between the electrodes 14 or 114.

When regenerable soybean tissue (including embryonic axes, excised or intact meristems, cotyledonary nodes, axillary buds, epicotyl segments, or similar tissues) is used as the target cells, the tissue must be physically secured to the target in such a fashion that the target may be inverted with the tissues being retained while also remaining viable. It has been found that using an agar-based medium or a medium with 8% xantham glue on the target surface is effective to hold the target tissue in place for the transformation.

For soybean tissues which are promptly transferred after treatment to a regeneration medium, a simple 1% to 5% water-agar medium may be used on the target surface. The agar formulation may then be plated in the bottom of small Petri dishes and allowed to harden. The tissues to be transformed may then be plated on the agar formulation, which will serve as the target surface.

Experimentation has revealed that for many transformations, a loading rate of 0.001 microgram to 40 microgram of DNA per milligram of gold carrier particles is appropriate. The DNA-coated particles are then applied to the carrier sheet at a loading rate of 0.00125 to 0.15 milligram of coated particles per square centimeter of the carrier sheet.

The entire assembly of the particle accelerator 10, or 110, and the target surface 22 may be partially evacuated so as to prevent the force of atmospheric drag from slowing the particles and/or the carrier sheet 18. Again this is done by surrounding the discharge chamber, the retaining screen and the target with a containment vessel. Although it is illustrated only in FIG. 1, the same containment vessel is used with the embodiments of FIGS. 4–6 and FIG. 7 to isolate the apparatus from the atmosphere. The vacuum should be only a partial vacuum since a high vacuum would desiccate the target plant tissues, rendering them non-viable. A vacuum of about 500 millimeters of mercury has been found sufficient and advantageous. Introduction of helium into the containment vessel is advantageous because helium, being of low density, does not carry the shock wave from the electric discharge to as great an extent, thus lessening shock wave damage to the plant tissues or the target. Also, the helium exerts less drag on the carrier sheet and the carrier particles than would air. Since the particle accelerator 10 or 110 is assembled in air, then evacuated with helium introduced into the containment vessel, air will be present in the discharge chamber 12 or 112 to efficiently carry the shock wave from the electric discharge to the carrier sheet 18, while helium will be present in the containment vessel. Placing a water film under the carrier sheet helps adhere it to the chamber so that air is retained in the discharge chamber 12 or 112.

The AC supply voltage is connected to the circuit of FIG. 6 to generate a high direct current voltage on the capacitor 32. The voltage may be varied somewhat, by adjustment of the variable transformer 26, depending on the tissue type and the spacing used. The variability of this voltage allows the force of the electric discharge, and thus the force applied to the carrier sheet 18, to be adjusted or tuned as needed for the species and tissue type of the target tissues. Voltages in the range of 4,000 to 30,000 volts have proved most successful in use with the apparatus of FIGS. 1 and 4–5. A high DC voltage is thus applied to the microfarad capacitor 32. By throwing the switch 36, the high voltage charge on the capacitor 32 is then applied between the electrodes 14 or 114.

In its operation, the apparatus of FIGS. 4–6 operates very such like the apparatus of FIG. 1. A spark discharge operation is initiated by the charging of the capacitor 32 with the total voltage charge on the capacitor being regulated by the setting on the autotransformer 26. When the switch 36 is thrown, a spark jumps the gap between the electrodes 114. The spark jumping between the electrodes vaporizes the water droplet 124 placed between the ends of the electrodes. The resulting explosive vaporization of the water droplet causes a shock wave within the interior of the spark discharge chamber 112 thereby propelling the carrier sheet 18 vertically upwards. The access cover 119 is also thrown upward by the shock wave but, since it is slightly heavier than the carrier sheet, it is accelerated more slowly and does not significantly detract from the force applied to the carrier sheet. In any event, the carrier sheet 18 is propelled vertically upward whereupon it engages the retaining screen 20 and remains fixed in place while the carrier particles layered thereon fly into the target 22.

The advantage of the apparatus of FIGS. 4 and 5 over that of FIG. 1 is that the direct force of the explosive shock wave does not contact the carrier sheet 18. The shock wave is tempered by the presence of the shield 113 which shields the carrier sheet 18 directly from the shock wave of the discharge. Instead the blast wave is reflected off of the other surfaces of the discharge chamber 112, from which it is directed toward the carrier sheet 18 as a sum of many overlapping wave fronts. The use of the removable access cover 119 and the carrier sheet 18 as covers for the interior of the discharge chamber 112 also provides another unique advantage, particularly when used in conjunction with helium in the vacuum containment vessel placed around the apparatus of FIGS. 4 and 5. The access cover 119 and the carrier sheet 18 are placed on the discharge chamber 112 in open air. Therefore, the interior of the spark discharge chamber, whether 12 or 112, is filled with normal air. After the carrier apparatus is placed in a vacuum containment, the vacuum can be drawn and the atmosphere in the chamber substituted with helium. The helium will therefore exist throughout the interior of the apparatus, except for the interior of the discharge chamber 112 which is still filled with air. Therefore, since the conduction of a shock wave is dependent on the density of the gas through which it travels, and since air is much denser than helium, the shock wave is relatively intense inside the discharge chamber 112 to provide the propulsive force to the carrier sheet 18. This effect could be made even more profound, if desired, by introducing an even more dense gas, such as a heavy inert gas like Xenon, into the interior of the spark discharge chamber. Once the carrier sheet 18 leaves the discharge chamber 112, it is surrounded substantially by an atmosphere of helium. Carrier sheet 18 therefore, as it moves, is subject to less drag, due to the lower density of helium, and the remaining shock wave from the explosion does not propagate out into the helium-filled remainder of the apparatus. Thus the full effect of the shock wave is used to propel the carrier sheet 18 while the target tissues are protected from unneeded or undesired contact by the shock wave from the spark discharge.

Shown in FIG. 7 is yet another alternative embodiment of the apparatus constructed in accordance with the present invention. The apparatus of FIG. 7 differs from the apparatus of FIG. 4 in that the spark discharge chamber 112 is generally perfectly rectangular without the slanted bottom sides of the spark discharge chamber 112 of FIG. 4. Other than that difference, the spark discharge chamber of FIG. 7 operates in a very analogous and similar fashion to that of the apparatus of FIGS. 1 and 4–6. This embodiment is included merely to illustrate that the particular geometry of the spark discharge chamber can be varied enormously as long as the chamber has within it the means to initiate the spark discharge necessary to make the shock wave for accelerated carrier sheet in accordance with the present invention.

The apparatus of FIGS. 4–6 and 7 have been used to genetically engineer a wide variety of organisms in addition to the pollen of plants. The apparatus has been used to create genetically engineered microorganisms, such as yeast, has been used to genetically engineer invertebrate animals, such as nematodes and has been used to transform the somatic cells of larger whole animals such as amphibians and mammals. In addition the apparatus has been used for a wide variety of other plants and has been successful in the creation of whole, intact, sexually mature plant lines of other species of plants such as soybean as well as trees, fruit bearing shrubs and other plants.

It is to be understood that the present invention is not limited to the particular configuration of the various apparatus and their methods of use disclosed in this application, but embraces all such modified forms thereof as come within the scope of the following claims.

What is claimed is:

1. A method of delivering genes into the cells of a plant comprising the steps of:

preparing copies of an expression vector appropriate for the plant including an exogenous coding region and flanking regulatory sequences effective to express the coding region in the cells of the plant;

coating the copies of the expression vector onto biologically inert carrier particles;

applying the coated carrier particles in a layer on a biologically inert carrier sheet;

placing the carrier sheet above a pair of spaced electrodes which have a gap between them bridged by a water droplet;

mounting a retaining screen spaced above the carrier sheet for retaining the carrier sheet after a selected upward distance of travel;

placing on a target surface above the retaining screen cells of the plant; and applying an electric voltage between the electrodes sufficient to generate an electric discharge between the electrodes vaporizing the water droplet, the shock wave from which accelerates the carrier sheet toward the retaining screen which retains the carrier sheet permitting the carrier particles to continue on to penetrate the cells of the plant, the force of the penetration being controlled by the voltage of the electric discharge.

2. A method as claimed in claim 1 wherein the carrier sheet is aluminized mylar.

3. A method as claimed in claim 1 wherein the carrier particles are applied to the carrier sheet by placing the carrier particles in ethanolic suspension which is placed on the sheet and then dried.

4. A method as claimed in claim 1 where the cells of the plant on the target surface is at least a portion of a plant.

* * * * *